(12) United States Patent
Tazawa

(10) Patent No.: US 11,304,849 B2
(45) Date of Patent: Apr. 19, 2022

(54) KNIFE FOR USE IN MEDICAL TREATMENT

(71) Applicant: MANI, Inc., Utsunomiya (JP)

(72) Inventor: Yoshiyuki Tazawa, Utsunomiya (JP)

(73) Assignee: MANI, INC., Utsunomiya (JP)

( * ) Notice: Subject to any disclaimer, the term of this patent is extended or adjusted under 35 U.S.C. 154(b) by 541 days.

(21) Appl. No.: 16/325,722

(22) PCT Filed: Aug. 24, 2017

(86) PCT No.: PCT/JP2017/030255
§ 371 (c)(1),
(2) Date: Feb. 15, 2019

(87) PCT Pub. No.: WO2018/043266
PCT Pub. Date: Mar. 8, 2018

(65) Prior Publication Data
US 2021/0330502 A1  Oct. 28, 2021

(30) Foreign Application Priority Data
Aug. 29, 2016  (JP) .............................. JP2016-166623

(51) Int. Cl.
*A61F 9/013* (2006.01)
(52) U.S. Cl.
CPC .... *A61F 9/0133* (2013.01); *A61F 2230/0017* (2013.01)
(58) Field of Classification Search
CPC ................ A61F 9/00736; A61F 9/0133; A61F 2230/0017; A61B 17/3205; A61B 17/3209; A61B 17/3211
See application file for complete search history.

(56) References Cited

U.S. PATENT DOCUMENTS

| 5,713,915 A | 2/1998 | Van Heugten et al. |
| 6,554,840 B2 | 4/2003 | Matsutani et al. |

(Continued)

FOREIGN PATENT DOCUMENTS

| JP | 2001238890 A | 9/2001 |
| JP | 2005103035 A | 4/2005 |

(Continued)

OTHER PUBLICATIONS

International Search Report (ISR) for Application No. PCT/JP2017/030255 dated Oct. 10, 2017.

(Continued)

*Primary Examiner* — Robert A Lynch
(74) *Attorney, Agent, or Firm* — Isshiki & Partners; Joseph P. Farrar

(57) ABSTRACT

A medical knife has a flat projection shape of a cutting part formed in an approximate rhomboid shape including a front end part, a widest part with the largest width, and a side surface part formed between the front end part and the widest part. A front side bevel constituting an edge on the front side and a back side bevel constituting an edge on the back side are individually formed, having as a boundary a virtual surface including an edge formed along the periphery of the cutting part. A ratio of the angle β between the virtual surface and the back side bevel to the angle α between the virtual surface and the front side bevel at the front end part is greater than the ratio of the angle θ between the virtual surface and the back side bevel to the angle α at the side surface part.

4 Claims, 4 Drawing Sheets

(56) References Cited

U.S. PATENT DOCUMENTS

2001/0029386 A1    10/2001  Matsutani et al.
2005/0070941 A1     3/2005  Isogimi
2011/0270292 A1*   11/2011  Saito .................. A61B 17/3209
                                                          606/167
2014/0031847 A1     1/2014  Mori et al.

FOREIGN PATENT DOCUMENTS

JP          1269299 B2    5/2009
JP       2012231842 A    11/2012
JP       2015142650 A     8/2015

OTHER PUBLICATIONS

Translation of the ISR for Application No. PCT/JP2017/030255 dated Oct. 10, 2017.
Written Opinion of the International Search Authority for Application No. PCT/JP2017/030255 dated Oct. 10, 2017.

\* cited by examiner (a)

(b)

(a)

(b)

(c)

(a)

(b)

(c)

(a)

(b)

KNIFE FOR USE IN MEDICAL TREATMENT

CROSS REFERENCE TO RELATED APPLICATIONS

The present application is a national phase entry under 35 U.S.C. § 371 of International Application No. PCT/JP2017/030255, filed Aug. 24, 2017, which claims priority from Japanese Application No. JP2016-166623, filed Aug. 29, 2016, the entire disclosures of which are hereby incorporated by reference herein.

TECHNICAL FIELD

The present invention relates to a medical knife designed to make an incision with a highly self-closing property in ophthalmic operations.

BACKGROUND ART

Making an incision with a highly self-closing property when inserting a medical knife in a spherical eyeball so as to incise the cornea or between the cornea and the sclera is regarded favorably in ophthalmic operations. An incision with a highly self-closing property is a gradually curved, so-called frown incision that becomes convex toward the center when viewing the eyeball from the front.

The medical knife used in ophthalmic operations may be a bevel-up type having a bottom surface that connects edges and having a trapezoidal cross-section with the bottom surface, or a bi-bevel type formed in a bead-like form having a line connecting edges at approximately the middle position, etc., wherein they are each selectively used.

The bevel-up type knife is characteristic of forces generated due to intraocular pressure and incision resistance differing on the top surface from on the lower surface, and a downward force increasing as incising progresses, thereby slipping towards the bottom surface overall. This knife is capable of making an incision having a relatively high self-closing property. On the other hand, the bi-level type knife is characteristic of forces acting on the top surface and the lower surface at the time of incision that are approximately equal, and insertion direction that is linear, thereby self-closing property of the formed incision is not very high.

Development of a medical knife that can make a more favorable incision is always in demand, whereby the medical knife described in Patent Document 1 has been proposed in response to this demand. This medical knife has been developed with the aim of making an incision having a highly self-closing property, wherein the vertex is a sharp pointed end formed in the front end portion of a cutting portion, and edges are formed up to a rhomboid-shaped, widest part.

Furthermore, first inclines having a surface including the edges as a border and slanted inward from the edges along the thickness on the upper part side, and second inclines connecting to the first inclines are formed, and a front surface on the uppermost part side is formed as an upper part flat surface. Moreover, lower side inclines having a surface including the edges as a border and slanted from the edges along the thickness on the lower part side toward the inner side of a cutting portion, and a flat surface connecting to the lower side inclines are formed. In particular, it is structured such that the thickness of the upper part side with a surface including the edges as a boundary is within a range of 75% to 93% of the total thickness of the cutting portion.

With the medical knife described above, when incising the cornea or between the cornea and the sclera, a force acting on the upper side that is generated due to intraocular pressure and incision resistance acting when a pointed end is inserted in the cornea on the spherical surface is larger than a force acting on the lower side but with little difference therebetween. Therefore, the incision when viewed from the inserting direction of the medical knife is a gradual curve that becomes convex upward. Furthermore, the incision when viewed from the front of the eyeball is a further gradual curve that becomes convex toward the center of the eyeball. Such an incision has a highly self-closing property, which is favorable.

PRIOR ART DOCUMENTS

Patent Documents

[Patent Document 1] Japanese Patent No. 4269299 (JP 2001-238890 A)

DISCLOSURE OF THE INVENTION

Problem to be Solved by the Invention

The medical knife described in Patent Document 1 can make an incision with a highly self-closing property in ophthalmic operations. However, the fact is that development of a medical knife that can make a better incision is always in demand.

The present invention aims to provide a medical knife capable of making an incision having a highly self-closing property.

Solution to the Problem

The medical knife according to the present invention for solving the above problems is a medical knife having an edge formed along the periphery of a cutting part. A flat projection shape of the cutting part is formed in an approximate rhomboid shape configured by a front end part including a pointed end formed on a front end portion of the cutting part and the vicinity of the pointed end, a widest part with the largest width, and a side surface part formed between the front end part and the widest part, a front side bevel constituting an edge on the front side and a back side bevel constituting an edge on the back side are individually formed, having as a boundary a virtual surface including an edge formed along the periphery of the cutting part, and the ratio of the angle between the virtual surface and the back side bevel to the angle between the virtual surface and the front side bevel at the front end part is greater than the ratio of the angle between the virtual surface and the back side bevel to the angle between the virtual surface and the front side bevel at the side surface part.

With the medical knife described above, thickness on the front side of the virtual surface as a boundary is preferably greater than thickness on the back side.

Moreover, with the medical knife described above, the ratio of the angle between the virtual surface and the back side bevel to the angle between the virtual surface and the front side bevels is nearly fixed at the side surface part preferably.

Advantageous Effect of the Invention

The medical knife (simply referred to as 'knife'hereafter) according to the present invention is capable of making an incision having a highly self-closing property.

The ratio of the angle between the back side bevel formed on the back side and the virtual surface, which includes an edge formed along the periphery of the cutting portion, to the angle between the front side bevel formed on the front side and the virtual surface is greater at the front end part than at the side surface part. Therefore, difference in forces generated from the front side to the back side due to intraocular pressure and incision resistance when incising an eyeball is smaller at the front end part and larger at the side surface part.

Accordingly, when incising an eyeball, force at the front end part trying to lower the knife to the back side is small but force trying to move straight is large, thereby allowing making a curved incision with a small curvature. Moreover, a force trying to lower the knife to the back side is larger at the side surface part than at the front end part, thereby allowing making a curved incision with a large curvature. An incision having a highly self-closing property may be formed as such.

In particular, setting the thickness on the front side of the virtual surface to be greater than the thickness on the back side, with a virtual surface including an edge as a boundary, allows a smaller difference between a force acting on the front side and a force acting on the back side when incising the eyeball.

Furthermore, setting the ratio of the angle between the virtual surface and the back side bevel to the angle between the virtual surface and the front side bevel to be a nearly fixed value at the side surface part allows the force acting on the side surface part trying to lower the knife to the back side to be a nearly fixed value when the knife is inserted in the eyeball. Therefore, a doctor can carry out a surgical operation stably.

DESCRIPTION OF EMBODIMENTS

Figure 1:
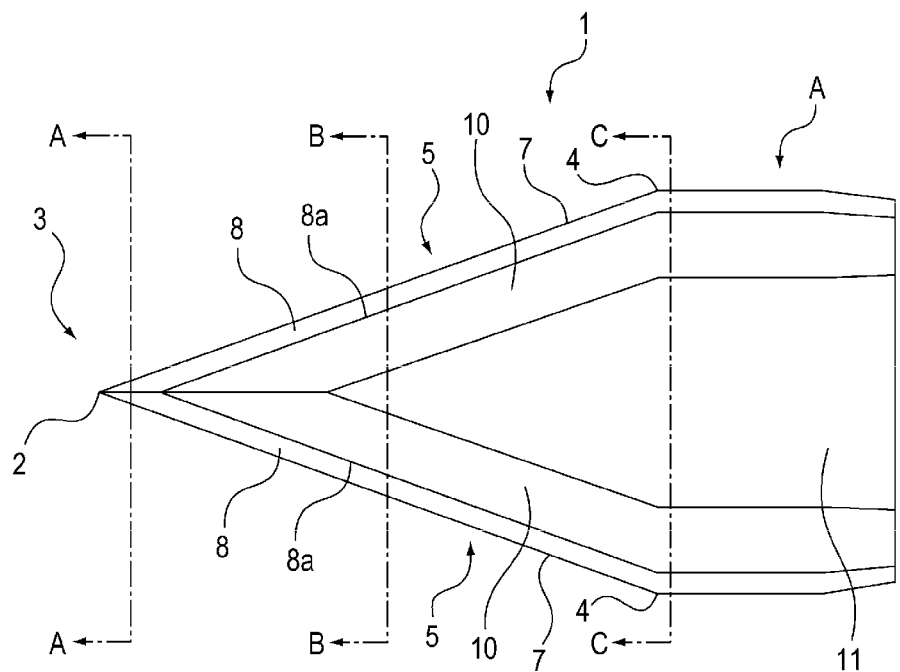
FIG. 1 illustrates a front surface and a back surface of a knife according to a first embodiment.
Figure 1:
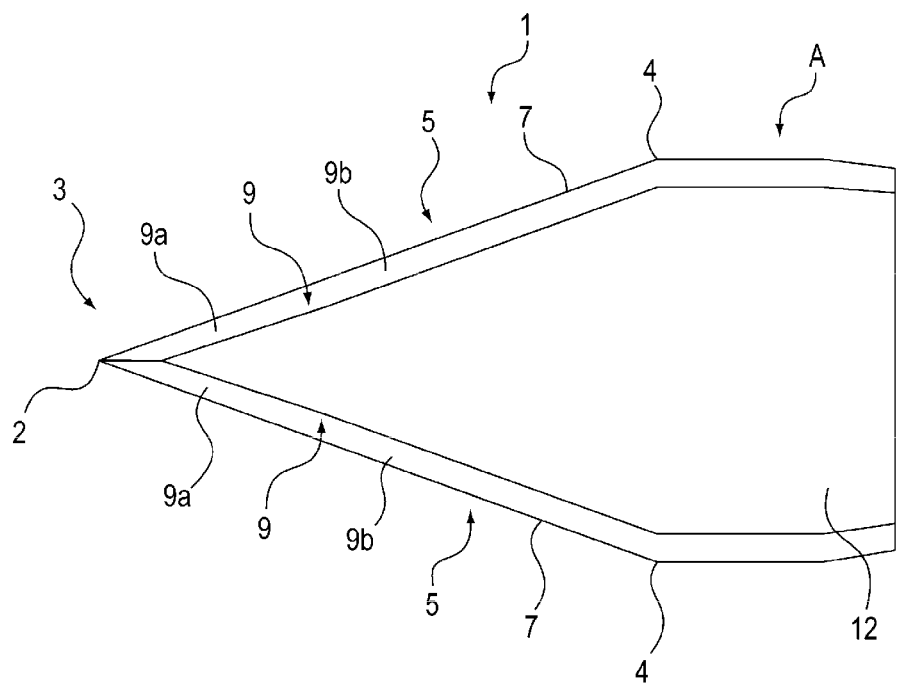

A knife according to the present invention is described below. The knife of the present invention is capable of making an incision having a highly self-closing property when incising an eyeball.

The knife of the present invention has functions of making an initial incision by insertion into an eyeball, and incising and expanding from the initial incision. In addition, it makes an incision long enough to allow insertion of a phacoemulsification device chip for aspirating the crystalline lens from the eyeball, and insertion of a lens to be embedded in the eyeball when performing an operation to embed the lens in the eyeball.

While the material constituting the knife according to the present invention is not particularly limited, steels such as stainless steel, carbon steel, etc. may be used. However, when considering rust prevention and processing easiness, use of stainless steel is favorable, wherein austenitic stainless steel is particularly preferred.

In the case of using austenitic stainless steel as a material, in order to increase hardness of the material, it is favorable to carry out cold plastic working at a predetermined processing rate so as to extend the structure into fibers, and carrying out pressing, polishing, and other necessary processing while maintaining the fibrous structure.

The knife of the present invention is formed into an approximately rhomboid shape, having a flat cutting portion made up of a front end part including a sharp pointed end and the vicinity of the pointed end, the widest part, and side surface parts formed between the front end part and the widest part. Edges (cutting blades) are formed in the outer periphery from the pointed end to the widest part. This allows insertion of the pointed end into the eyeball and moving it straight in so as to make an incision corresponding to the size of the widest part. Furthermore, by inserting the pointed end into the eyeball and moving left and right, an incision having a desired width can be formed regardless of the size of the widest part.

With the knife of the present invention, the vicinity of the pointed end constituting the front end part is assumed, within a triangle having the pointed end as a vertex and a line connecting the edges of the widest part as a base, to range until ½ the length of a perpendicular line (also referred to as an axis) from the pointed end to the base, preferably ¼ thereof. If the length of the vicinity of the pointed end including the pointed end constituting the front end part exceeds ½ the length of the perpendicular line from the pointed end to the base, the incision will be similar to that made by the conventional bi-bevel type knife, and thus be unfavorable. On the other hand, if it is approximately 1/30 or less the length of the perpendicular line from the pointed end to the base, the range allowing the knife to move straight when beginning incision is narrower, whereby an incision having a highly self-closing property cannot be formed.

Furthermore, the knife according to the present invention is assumed to have a virtual surface including paired edges formed along the circumference of the cutting portion having the pointed end as a vertex, wherein front side bevels are formed on the front side with the virtual surface as a boundary, and back side bevels are formed on the back side. In addition, the ratio of the angle between the virtual surface and the back side bevels to the angle between the virtual surface and the front side bevels at the front end part (the ratio of angles at the front end part) is greater than the ratio of the angle between the virtual surface and the back side bevels to the angle between the virtual surface and the front side bevels at the side surface parts (the ratio of angles at the side surface parts).

How much larger the ratio of angles at the front end part is greater than the ratio of angles at the side surface parts is not particularly limited; however, when performing an ophthalmic operation, the ratio should favorably be a value that allows sufficiently linear movement at the front end part and allows a moderate downward force to act on the side surface parts. That is, it is preferable to set such a preferable ratio such that characteristics of the bi-bevel type knife at the front end part and characteristics of the bevel-up type knife at the side surface parts are provided.

The case of making the ratio of angles at the front end part larger than the ratio of angles at the side surface parts is possible by setting as independent angles the angle between the virtual surface and the front side bevels at the front end part, the angle between the virtual surface and the back side bevels at the front end part, the angle between the virtual surface and the front side bevels at the side surface parts, and the angle between the virtual surface and the back side bevels at the side surface parts.

For example, implementation is possible by fixing the angle between the virtual surface and the front side bevels at the front end part and the side surface parts, and setting the angle between the virtual surface and the back side bevels at the front end part to be larger than the angle between the virtual surface and the back side bevels at the side surface parts. Alternatively, implementation is also possible by making the angle between the virtual surface and the front side bevels at the front end part smaller than the angle between the virtual surface and the front side bevels at the side surface parts, and fixing the angle between the virtual surface and the back side bevels at the front end part and the side surface parts.

Moreover, it is preferable that the thickness of the front side is thicker than the back side with the virtual surface as a boundary. How much thicker the thickness of the front side is than the thickness of the back side is not particularly limited; however, a thickness allowing an acting downward force to make an incision having a self-closing property is preferred.

Further, it is preferable to make nearly fixed the ratio of the angle between the virtual surface and the back side bevels at the side surface parts to the angle between the virtual surface and the front side bevels. In this case, difference between the force acting on the front side of the side surface parts and force acting on the back side is nearly fixed. Therefore, measurements of movement toward the back surface when inserted by unit length are nearly fixed, thereby making it possible to make an incision made up of a curved line having a stable curvature.

A first embodiment of the knife is described next using FIGS. 1 to 3. The knife according to this embodiment has a fixed angle between the virtual surface and the front side bevels at the front end part and the side surface parts, wherein the angle between the virtual surface and the back side bevels at the front end part is set larger than the angle between the virtual surface and the back side bevels.

In the drawings, a knife A is constituted by a cutting portion 1 and a shank, omitted from the drawing, connecting to the cutting portion 1. The cutting portion 1 has a sharp pointed end 2, and a front end part 3 including the pointed end 2 and the vicinity of the pointed end 2. Furthermore, a widest part 4 of the cutting portion 1 is formed at a position apart from the pointed end 2, and portions between the front end part 3 and the widest part 4 are formed as side surface parts 5.

Distance from the pointed end 2 to the widest part 4, detailed measurements of width etc. of the widest part 4, and range of the front end part 3 are variously set in accordance with purpose of the knife A or, for example, specifications such as size of incision etc.

Paired edges 7 are formed along the periphery of the cutting portion 1 from the pointed end 2 as a vertex to the widest part 4. These edges 7 have a function of cutting open biotissue, and are formed by front side bevels 8, which are formed on the front side, and back side bevels 9, which are formed on the back side, with a virtual surface 7a as a boundary including the paired edges 7 that are formed along the periphery of the cutting portion 1. Since the front side bevels 8 and the back side bevels 9 form the edges 7 together, they are formed as very smooth ground surfaces.

Second bevels 10 are formed along the front side bevels 8 that are formed on the front side of the cutting portion 1, and boundary lines 8a are formed at the boundaries of the bevels 8 and 10. Accordingly, the second bevels 10 are formed between the front side bevels 8 constituting both of the edges 7. Since the second bevels 10 do not function as cutting blades, they do not need to be formed with a very smooth ground surface, and thus may be pressed surfaces or rough ground surfaces.

Moreover, a front side flat surface 11 is formed between the paired second bevels 10 along the paired second bevels 10. This front side flat surface 11, as with the second bevels 10, may also be a pressed surface or rough ground surface.

Note that while the second bevels 10 and the front side flat surface 11 are provided in this embodiment, the second bevels 10 and the front side flat surface 11 are not requirements, and a structure excluding these surfaces is possible. For example, the front side bevels 8 may be extended toward the center of the cutting portion 1, crossing at the center, or otherwise the second bevels 10 may be extended toward the center of the cutting portion 1, crossing at the center. The surfaces to be extended in those cases may be either flat or curved.

A back side flat surface 12 is formed between the paired back side bevels 9 formed on the back side of the cutting portion 1, connecting to the paired back side bevels 9. The back side flat surface 12 is formed as a surface not functioning as a cutting blade, similarly to the aforementioned second bevels 10 and the front side flat surface 11. Therefore, it does not need to be formed as a very smooth ground surface, and may be a rough ground surface or a pressed surface.

The front end part 3 is formed including the pointed end 2 and the vicinity thereof. The range of the vicinity of the pointed end 2 is not limited, but preferably allows formation of an appropriate incision for demonstrating a self-closing property required in ophthalmic operations.

In this embodiment, a line (line C-C in (a) of FIG. 1) running across the widest part 4 is set as a base, and the range of approximately ⅕ the measurements from the pointed end 2 to the base on a perpendicular line (axis) passing through the pointed end 2 is set as the front end part 3. However, this range is not to be limited, and it may be longer or shorter.

As mentioned above, in this embodiment, the angles between the virtual surface 7a and the front side bevels 8 at the front end part 3 and the side surface parts 5 are fixed. In addition, the angle between the virtual surface 7a and the back side bevels 9a at the front end part 3 are set larger than the angle between the virtual surface 7a and the back side bevels 9b at the side surface parts 5.

In particular, a transition region is formed as a smooth curved surface so as to allow continuous transition from the back side bevels 9a constituting the front end part 3 to the back side bevels 9b constituting the side surface parts 5.

The relationship between the angle between the virtual surface 7a and the front side bevels 8 at the front end part 3 and the angle between the virtual surface 7a and the back side bevels 9 (9a and 9b) with the virtual surface 7a at the front end part 3 and the side surface part 5 as a boundary is described next.

Figure 2:
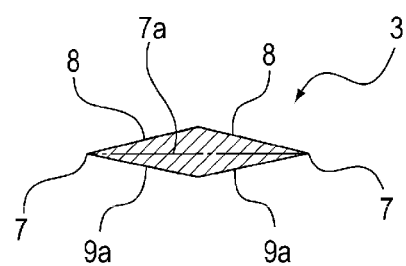
FIG. 2 illustrates partial cross-sectional views of FIG. 1.
Figure 2:
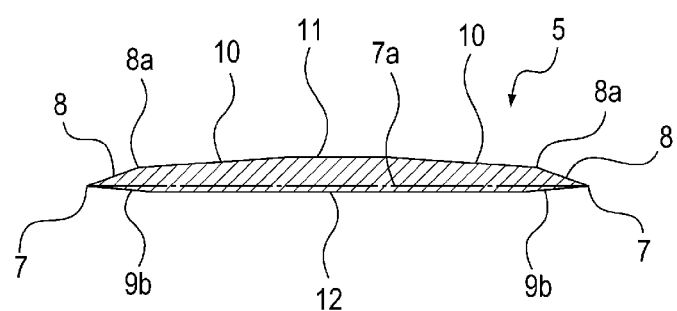
Figure 2:
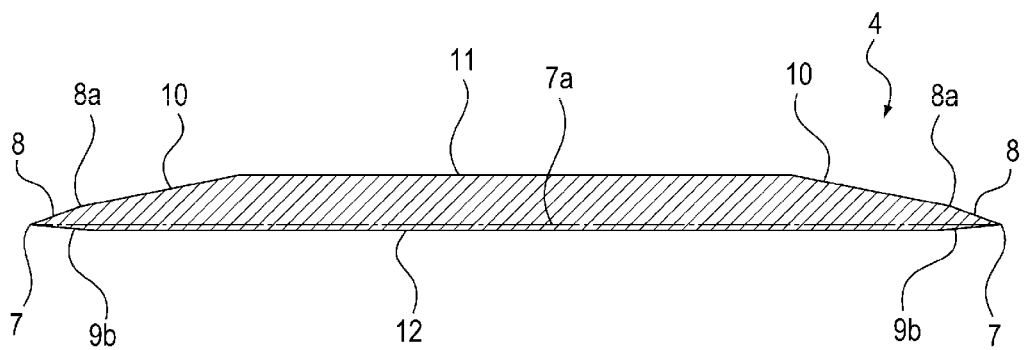
Figure 3:
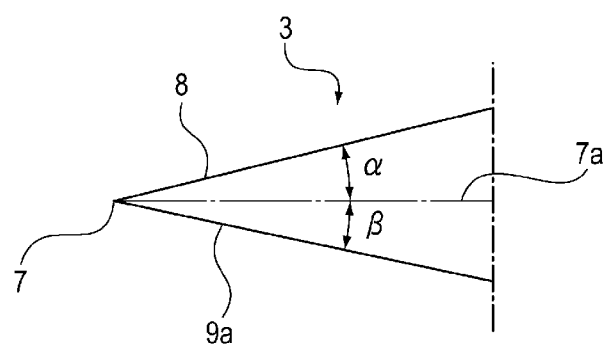
FIG. 3 illustrates enlarged views of an edge portion.
Figure 3:
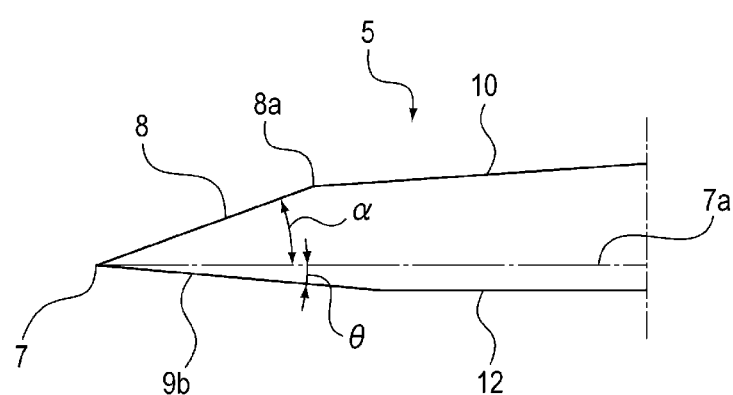
Figure 3:
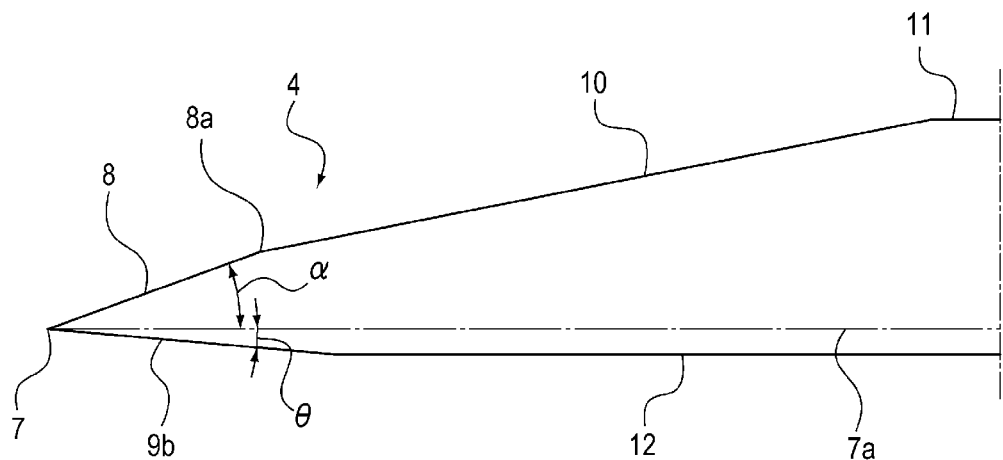

It can be seen that (a) of FIG. 2 is a cross-sectional view of the front end part 3 cut along a line A-A, and (a) of FIG. 3 is an enlarged explanatory drawing of the edge 7. Also, (b) of FIG. 2 is a cross-sectional view of the side surface part 5 cut along a line B-B, and (b) of FIG. 3 is an enlarged explanatory drawing of the edge 7. In addition, (c) of FIG. 2 is a cross-sectional view of the widest part 4 cut along a line C-C, and (c) of FIG. 3 is an enlarged explanatory drawing of the edge 7.

As illustrated in the drawings, the edges 7 at the front end part 3 are constituted by the front side bevels 8 crossing the virtual surface 7a at an angle $\alpha$ and the back side bevels 9a crossing the virtual surface 7a at an angle $\beta$, wherein the virtual surface 7a is a boundary.

Moreover, the edges 7 at the side surface part 5 are constituted by the front side bevels 8 crossing the virtual surface 7a at an angle α and the back side bevels 9b crossing the virtual surface 7a at an angle θ, wherein the virtual surface 7a is a boundary. Furthermore, the edges 7 at the widest part 4 are constituted by the front side bevels 8 crossing the virtual surface 7a at an angle α and the back side bevels 9 crossing the virtual surface 7a at an angle θ, wherein the virtual surface 7a is a boundary.

Values of the angles α, β, and θ are not limited. However, the angle β is set to be greater than the angle θ. That is, the ratio of the angle β between the virtual surface 7a and the back side bevels 9a at the front end part 3 to the angle α between the virtual surface 7a and the front side bevels 8 at the edges 7 to is β/α. Moreover, the ratio of the angle θ between the virtual surface 7a and the back side bevels 9b at the side surface part 5 to the angle α between the virtual surface 7a and the front side bevels 8 at the edges 7 to is β/α. Accordingly, the ratio β/α at the front end part 3 is greater than the ratio β/α at the side surface part 5.

Since the ratio β/α is greater than the ratio θ/α, difference in force acting on the front end part 3 between on the front side and on the back side is smaller than difference in force acting on the side surface part 5 between on the front side and on the back side when piercing an eyeball using the knife A. Accordingly, when the knife A is inserted straight into an eyeball, it can be moved approximately linearly at the front end part 3 so as to incise, and incising while the knife A is moving (downward) toward the back side as it is transitioned from the front end part 3 to the side surface part 5 is possible.

As a result, when the incision formed in the eyeball is viewed from the front, the incision at the front end part 3 is a gradual curved shape, and the incision at the side surface part 5 is a downward curve with a large curvature. Moreover, a frown incision can be realized by such an incision.

The inventors of the present invention have constructed a knife having the widest part 4 set to 2.4 mm, axial measurement from the pointed end 2 to the widest part 4 set to 3.0 mm, measurement of the front end part 3 from the pointed end 2 in the axis direction set to approximately 0.5 mm, measurement of the side surface part 5 connecting to the front end part 3 set to approximately 2.5 mm, the angle between the paired edges 7 set to approximately 60 degrees with the pointed end 2 as a vertex, the angle α between the virtual surface 7a and the front side bevels 8 at the front end part 3 set to approximately 21.5 degrees, the angle β between the virtual surface 7a and the back side bevels 9a set to approximately 11.5 degrees, the angle α between the virtual surface 7a and the front side bevels 8 set to approximately 21.5 degrees, and the angle θ between the virtual surface 7a and the front side bevels 9b set to approximately 9.5 degrees.

With this knife, the ratio β/α at the front end part 3 is 0.53, and the ratio θ/α at the side surface part 5 is 0.44. Accordingly, the ratio β/α at the front end part 3 is greater than the ratio θ/α at the side surface part 5.

Upon conducting an experiment of making an incision in a pig's eyeball using the knife configured as described above, the incision from the pointed end 2 to the front end part 3 is a gradual curved shape with a small curvature, and the incision of the side surface part 5 has a larger curvature than the aforementioned incision. It is concluded that the incision that has been achieved in this experiment is a sufficiently favorable frown incision.

Figure 4:
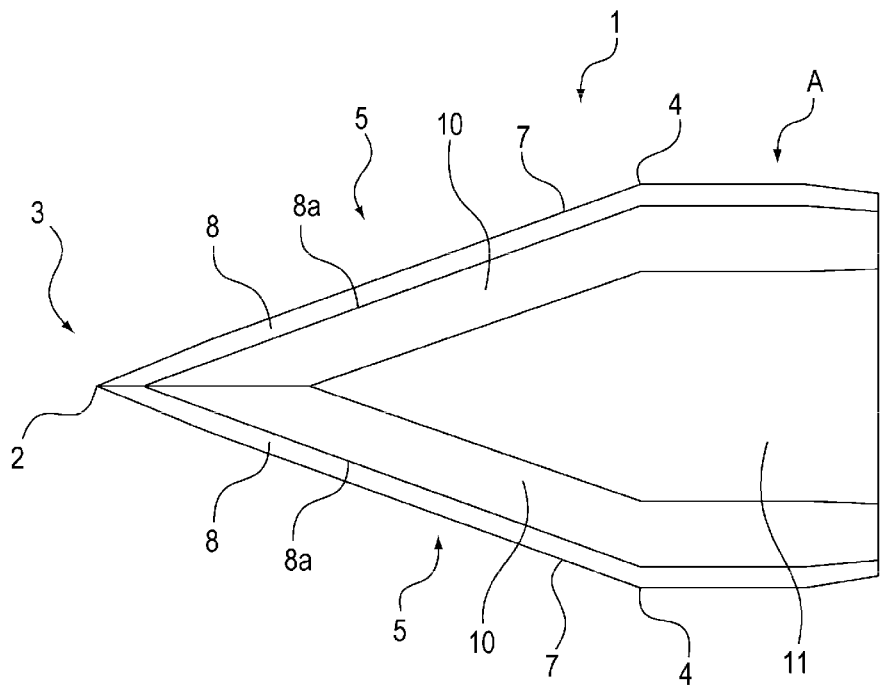
FIG. 4 illustrates a front surface and a back surface of a knife according to a second embodiment.
Figure 4:
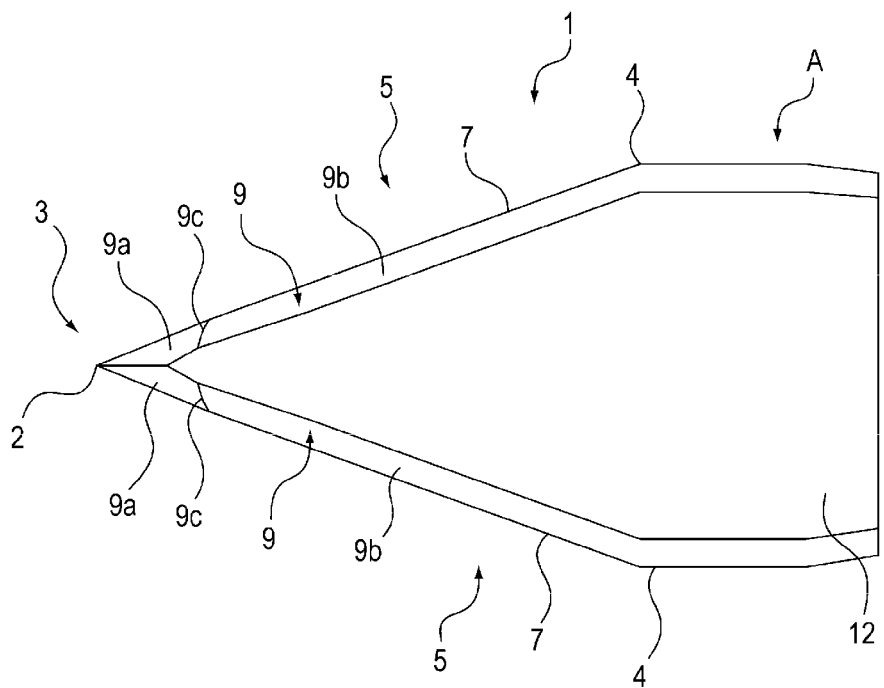

Next, configuration of the knife A according to a second embodiment is described using FIG. 4. Note that the same portions and portions having the same functions as in the first embodiment are given the same reference numerals in the drawing and description thereof is omitted.

In this embodiment, a boundary line 9c is formed in a region of the back side bevels 9 that transitions from the back side bevels 9a constituting the front end part 3 to the back side bevels 9b constituting the side surface part 5. That is, the back side bevels 9a of the front end part 3 and the back side bevels 9b at the side surface part 5 are not continuously connected, but are connected via the boundary line 9c formed specifically. Such back side bevels 9a and 9b may be made by inclining and grinding the material of the knife on the basis of the preset angles β and θ with a grinding material having a high rigidity.

Even if the back side bevels 9a and 9b are connected via the boundary line 9c as described above, the formed incision also has a gradual curved shape with a small curvature at the front end part 3, and has a larger curvature than the aforementioned incision at the side surface part 5 without impact on penetrating property when incising.

Note that this embodiment has a configuration such that the boundary line 9c is formed in a region of the back side bevels 9 that transitions from the back side bevels 9a constituting the front end part 3 to the back side bevels 9b. However, when making the ratio β/α at the front end part 3 greater than the ratio β/α at the side surface part 5 by changing angles of the front side bevels 8 within the range corresponding to the front end part 3 and range corresponding to the side surface part 5, it is obvious that the front part end 3 and the side surface parts 5 of the front side bevels 8 may be connected via the boundary line.

INDUSTRIAL APPLICATION

The knife A according to the present invention is applicable when making an incision having a highly self-closing property in ophthalmic operations.

EXPLANATION OF REFERENCE NUMERALS

A: Knife
1: Cutting portion
2: Pointed end
3: Front end part
4: Widest part
5: Side surface part
7: Edge
7a: Virtual surface
8: Front side bevel
9, 9a, 9b: Back side bevel
9c: Boundary line
10: Second bevel
11: Front side flat surface
12: Back side flat surface

The invention claimed is:
1. A medical knife having an edge formed along the periphery of a cutting part, comprising:
a flat projection shape of the cutting part is formed in a five-sided polygon shape of which one side is connected to a shank, and is configured by a front end part including a pointed end formed on a front end portion of the cutting part and the vicinity of the pointed end, a widest part with the largest width, and a side surface part formed between the front end part and the widest part,
a front side bevel constituting an edge on the front side and a back side bevel constituting an edge on the back side are individually formed, having as a boundary a virtual surface including the edge formed along the periphery of the cutting part, and the ratio of the angle between the virtual surface and the back side bevel to the angle between the virtual surface and the front side bevel at the front end part is greater than the ratio of the angle between the virtual surface and the back side bevel to the angle between the virtual surface and the front side bevel at the side surface part.

2. The medical knife of claim 1, wherein a thickness on the front side of the virtual surface is greater than a thickness on the back side, with flail the virtual surface as a boundary.

3. The medical knife of claim 2, wherein the ratio of the angle between the virtual surface and the back side bevel to the angle between the virtual surface and the front side bevel is nearly fixed at the side surface part.

4. The medical knife of claim 1, wherein the ratio of the angle between the virtual surface and the back side bevel to the angle between the virtual surface and the front side bevel is nearly fixed at the side surface part.

\* \* \* \* \*